United States Patent [19]

Stiefel et al.

[11] Patent Number: 4,547,321

[45] Date of Patent: Oct. 15, 1985

[54] COMPOUNDS CONTAINING THE $[CO(MOS_4)_2]^{3-}$ TRIANION AND THEIR PREPARATION

[75] Inventors: Edward I. Stiefel, Bridgewater; Wie-Hin Pan, Fanwood, both of N.J.; Stephen McKenna, Oakland, Calif.

[73] Assignee: Exxon Research and Engineering Co., Florham Park, N.J.

[21] Appl. No.: 518,362

[22] Filed: Jul. 29, 1983

[30] Foreign Application Priority Data

Apr. 29, 1983 [GB] United Kingdom ............... 8311906

[51] Int. Cl.⁴ .................... C07F 11/00; C07F 15/06
[52] U.S. Cl. ................................ 556/14; 556/3; 556/28
[58] Field of Search .............. 423/511; 260/429 R, 260/439 R

[56] References Cited

U.S. PATENT DOCUMENTS 2,770,527 11/1956 Alderson, Jr. et al. ............. 423/511

OTHER PUBLICATIONS

Müller et al, Angew. Chem. Int. Ed. Engl. 16 pp. 705–706 (1977).
Müller Z. Anorg. Allg. Chem. 483 pp. 69–74 (1981), Chem. Abst. 96 114897k.
Chemical Abstracts 87 192950a (1977).

*Primary Examiner*—Helen M. S. Sneed
*Attorney, Agent, or Firm*—Edward M. Corcoran

[57] ABSTRACT

Compositions of the formula $[(Cat^n)]_{3/n}[Co(MoS_4)_2]$ wherein Cat is a mono, di or trivalent cation and n is 1, 2 or 3, respectively, have been prepared in non-aqueous media. The $[Co(MoS_4)_2]^{3-}$ anion has the general structure

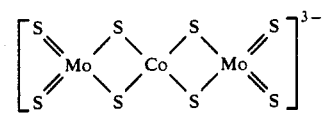

Cat is preferably an alkyl substituted quaternary ammonium compound.

15 Claims, No Drawings

COMPOUNDS CONTAINING THE [CO(MOS$_4$)$_2$]$^{3-}$ TRIANION AND THEIR PREPARATION

BACKGROUND OF THE INVENTION

1. Field of the Invention

This invention relates to salts of the [Co(MoS$_4$)$_2$]$^{3-}$ trianion and their preparation wherein the cobalt is four coordinated with the two tetrathiomolybdate groups. More particularly this invention relates to compounds of the formula [Cat$^n$]$_{3/n}$[Co(MoS$_4$)$_2$] wherein Cat is a mono, di or trivalent cation, n is 1, 2 or 3 and wherein the cobalt is tetracoordinated with four sulfur atoms with each of the two thiomolybdate groups providing two of the four sulfur atoms.

BACKGROUND OF THE DISCLOSURE

It is known to those skilled in the art that two tetrathiomolybdate or two tetrathiotungstate ligands are capable of chelating a single transition element such as Ni, Zn, Pd, or Pt. Thus, U.S. Pat. No. 4,256,817 discloses compounds of the formula [Cat$^{n+}$]$_{2/n}$[Ni(WS$_4$)$_2$] wherein the nickel is tetracoordinated with four sulfur atoms with each of the two thiotungstate groups providing two of said four sulfur atoms, said sulfur atoms acting as ligands to coordinately bond the nickel to each of the two tetrathiotungstate groups. Müller and coworkers reported the compounds [(C$_6$H$_5$)$_4$P]$_2$[Ni(MoS$_4$)$_2$], and [(C$_6$H$_5$)$_4$P]$_2$[Zn(MoS$_4$)$_2$] (A. Müller, E. Ahlborn and H. -H. Heinsen Z. Anorg. Allg. Chem., 386 102 (1971)) and [(C$_6$H$_5$)$_4$P]$_2$[Ni(WS$_4$)$_2$], [(C$_6$H$_5$)$_4$P]$_2$[Zn(WS$_4$)$_2$] and [(C$_6$H$_5$)$_4$P]$_2$[Co(WS$_4$)$_2$] (A. Müller, E. Diemann and H. -H. Heinsen, Chem. Ber., 104 975 (1971)). The structure of [(C$_6$H$_5$)$_4$P]$_2$[Co(WS$_4$)$_2$] which contains four-coordinated tetrahedral cobalt with four sulfur donor atoms provided two each by the two tetrathiotungstate ions was reported in 1978 by Müller and S. Sarkar, *Angew, Chem. Int. Ed. Engl.* 16 705 (1977). However, prior to the instant invention no one has been able to make the cobalt tetrathiomolybdate trianion of the formula [Co(MoS$_4$)$_2$]$^{3-}$ wherein the cobalt is tetrahedrally coordinated with four sulfur atoms with each of the two tetrathiomolybdate groups providing two of said four sulfur atoms.

SUMMARY OF THE INVENTION

Compositions of matter containing the cobalt bis(tetrathiomolybdate) [Co(MoS$_4$)$_2$]$^{3-}$ trianion of the structure

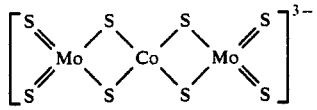

have now been prepared in non-aqueous media. In these compositions the molybdenum remains in the 6+ oxidation state of the tetrathiomolybdate and the cobalt is in the 1+ oxidation state. More particularly, this invention relates to compositions of matter of the formula [Cat$^n$]$_{3/n}$[Co(MoS$_4$)$_2$] wherein Cat is a mono, di or trivalent cation and n is 1, 2 or 3 respectively and wherein the cobalt is tetra-coordinated with four sulfur atoms with each of the two tetrathiomolybdate groups providing two of each of said four sulfur atoms. Cat may be an onium cation of the formula [XH$_a$R$_{4-a}$] wherein X is N, As or P, a is 0, 1, 2, 3 or 4 and R is an alkyl or aryl group or mixture thereof. If X is As or P, then R will preferably be an aryl group. Cat may also be a sulfonium cation of the formula (SO)H$_b$R$_{3-b}$ or SH$_b$R$_{3-b}$ wherein b is 0, 1, 2 or 3 and R is an alkyl or aryl group or mixture thereof, preferably an aryl group.

Preferably Cat will be an ammonium or substituted ammonium cation NH$_a$R$_{4-a}$ wherein a is 0, 1, 2, 3 or 4 and wherein R comprises an alkyl or aryl group or mixture thereof. More preferably, Cat will be a tetraalkyl ammonium cation, NR$_4^+$.

The compositions of this invention may be prepared using cobalt compounds wherein the cobalt is in the monovalent or 1+ oxidation state or in higher oxidation states. However, if one starts with cobalt compounds wherein the cobalt is in an oxidation state greater than 1+, then sufficient reducing agent must be present in the reaction media to reduce the cobalt present therein to the monovalent oxidation state, (Co$^+$). In any event, it is important that the compounds of this invention be formed in media that is inert or net reducing and, more preferably, anaerobic.

These compounds have been found to be useful hydrotreating catalyst precursors. These compounds form green solutions which turn black when exposed to oxygen. Thus, these compounds are also useful as oxygen indicators and oxygen sensitive dyes. They should also be useful for stabilizing organic substrate materials to light as set forth in U.S. Pat. No. 4,256,817.

DETAILED DESCRIPTION OF THE INVENTION

Compounds of the formula [Cat$^n$]$_{3/n}$[Co(MoS$_4$)$_2$] containing the cobalt bis(tetrathiomolybdate) trianion [Co(MoS$_4$)$_2$]$^{3-}$ of the structure set forth above wherein the cobalt is in the monovalent oxidation state and n is 1, 2 or 3 have been prepared in non-aqueous media using mono, di and trivalent cobalt-containing compounds. If the cobalt in the cobalt-containing starting material is in the monovalent oxidation state (Co$^+$), a reducing agent need not be present in the reaction media. However, a non-oxidizing environment is essential to form the trianion in significant amounts irrespective of whether the cobalt in the starting material is in the mono, di or trivalent state.

When using a cobalt-containing starting material wherein the cobalt is di- or trivalent, it is necessary for the cobalt to be converted to the monovalent form during the reaction in order for the product to be formed. The conversion into the monovalent cobalt form can be effected by the presence of sufficient reducing agent in the reaction media. The reducing agent may be added to the reaction media or it may be part of the cobalt containing compound used as one of the starting materials. When a compound containing monovalent cobalt is used, no reducing agent need be present in the reaction medium. However, regardless of the cobalt starting material used, it is essential that the reaction is carried out in a non-oxidizing environment.

The cation (Cat) may be a mono, di or trivalent organic onium cation of the type disclosed in U.S. Pat. No. 4,256,817, the disclosures of which are incorporated herein by reference. Illustrative, but non-limiting examples include ammonium and substituted ammonium cations [NH$_a$R$_{(4-a)}$]$^+$ wherein a is 0, 1, 2, 3 or 4 and wherein R is an alkyl group, aryl group or mixture thereof and preferably an alkyl group. In a particularly preferred embodiment Cat will be a quaternary ammonium cation, $(NR_4)^+$, wherein R is an alkyl group. Other examples of useful monovalent organic onium cations include phosphonium cations $[PR_4]^+$, arsonium cations $[AsR_4]^+$, sulfonium cations $SR_3^+$ and sulfoxonium cations $SR_3O^+$ wherein R is one or more alkyl or aryl groups or combination thereof. More complex mono cations such as $[(C_6H_5)_3PNP(C_6H_5)_3]^+$ are also effective. Divalent organic bis(onium) cations are also useful such as ethylenediammonium $(H_3NCH_2CH_2NH_3)^{2+}$ and ethylenediphosphonium $(R'_3PCH_2CH_2PR''_3)^{2+}$ wherein R' and R'' are the same or different and comprise an alkyl group, an aryl group and mixtures thereof.

Cat may also be a mono or divalent alkali or alkaline earth metal or mixture thereof as well as a mono, di or trivalent transition metal-containing complex cation. By transition metal containing complex cation is meant a composition containing a transition metal which is coordinated by organic ligands, said organic ligands containing atoms such as O, N, S or P which are coordinately bound to the transition metal. Illustrative, but non-limiting examples of such cations include [Fe(ethylenediamine)$_3$]$^{2+}$, [Cr(NH$_3$)$_6$]$^{3+}$ and [Ni(2,2'-bipyridine)$_3$]$^{2+}$.

Illustrative, but non-limiting examples of monovalent cobalt starting materials useful for forming the new composition of this invention include cyclopentadienyl cobalt dicarbonyl—$(C_5H_5)Co(CO)_2$, hydridocobalt tetracarbonyl—$HCo(CO)_4$ and cyclopentadienyl cobalt cyclooctatetraene—$(C_5H_5)Co(C_8H_8)$.

When a compound containing a divalent or trivalent cobalt atom is used as a starting material it is necessary for the cobalt to be converted to the monovalent from during the formation of the bis(tetrathiomolybdate) trianion. The following reaction sequence illustrates the formation of $[Cat^n]_{3/n}[Co(MoS_4)_2]$ from $CoCl_2$ and $[Cat^n]_{2/n}(MoS_4)$ in the presence of a reducing agent such as an organic thiolate, $SR^-$, wherein R and R' are the same or different and comprise an alkyl or aryl group.

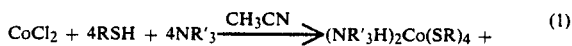

(1)

(2)

$[(Cat^n)_{3/n}][Co(MoS_4)_2] + \frac{1}{2} RSSR + 2(NR'_3H)SR + [(cat^n)_{1/n}] SR$ Thus when the simple salt $CoCl_2$, where the cobalt is divalent, is used as a starting material, it is first reacted with a thiolate reagent, $SR^-$, to form the anion $Co(SR)_4^{2-}$. The thiolate reagent $SR^-$ is generated by reacting the thiol RSH with a base. Although any base may be used, such as NaOH, it is preferred to use a nitrogen containing organic base such as pyridine, or a primary, secondary or tertiary amine. In equation (1) above, the base is a trialkylamine. Although only a stoichiometric amount of reducing agent $SR^-$ is needed to effect the reduction from $Co^{2+}$ to $Co^+$, it is preferred to use an excess of reducing agent. The solution containing the anion $Co(SR)_4^{2-}$ is then added to the $(Cat^n)_{2/n}MoS_4$, partially dissolved in $CH_3CN$ (Eq. 2). After a period of 30 to 60 minutes, the reaction is complete. Since the product $[(Cat^n)_{3/n}][Co(MoS_4)_2]$ is the least soluble in the reaction mixture, it can be readily precipitated out of the solution by adding diethylether to the reaction mixture. If only two equivalents of thiol are added, the reaction may still proceed but the yields of the desired product will be low.

When the cobalt starting material already contains the reducing agent bonded to it, for example, $Co(S_2CNR_2)_3$, it can be directly reacted with $(NH_4)_2MoS_4$. Equation 3 illustrates this reaction.

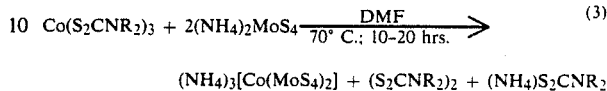

(3)

$(NH_4)_3[Co(MoS_4)_2] + (S_2CNR_2)_2 + (NH_4)S_2CNR_2$

In this example, the cobalt starting material has cobalt in the trivalent state. Three equivalents of the reducing agent, N,N-dialkyl dithiocarbamate, $(S_2CNR_2)^-$, in this material, are coordinated with the $Co^{3+}$ in this complex. In this reaction, N,N-dimethylformamide is the preferred solvent. Further, this reaction requires heating at 70° C. and at least 10 hours for the reaction to give significant yield of the product. The reducing agent gets oxidized to tetraalkylthiuramdisulfide $(S_2CNR_2)_2$ as the $Co^{3+}$ gets converted to $Co^{1+}$. Examples of other reducing agents that are capable of coordinating with cobalt include alkyl or aryl xanthates $(S_2COR^-)$, o,o-dialkyldithiophosphates $(S_2P(OR)_2^-)$, dialkyldithiophosphinates $(S_2PR_2^-)$ or thiolates $(SR^-)$, wherein R is an alkyl group, aryl group or mixture thereof.

It should be understood that other reducing agents such as dithionite, borohydrides, hydrazines, etc. can be used as the reductant in this synthesis route when other cobalt $2+$ or $3+$ compounds or complexes are used as the cobalt starting material. These include complex ions in which N, O, S or P are coordinated to the cobalt atom. Illustrative, but non-limiting examples of other suitable cobalt $2+$ and $3+$ compounds and complexes include salts of $Co(amine)_6^{2+,3+}$ $Co(acetylacetonate)_3$, salts of $[Co(NH_3)_5Cl]^{2+}$, etc.

The cobalt bis(tetrathiomolybdate) trianion compounds of this invention were analyzed using a variety of analytical techniques. Thus, elemental composition was determined by using combustion analysis for carbon, nitrogen, hydrogen and sulfur while atomic absorption spectroscopy was used to analyze for the metals. Infrared and electronic absorption spectroscopy were also employed as well as magnetic susceptibility and X-ray powder diffraction spectroscopy. In the infrared region, characteristic bands of the trianion of this invention, $[Co(MoS_4)_2]^{3-}$, were observed at 481 cm$^{-1}$, 466 cm$^{-1}$ and at 445 cm$^{-1}$. In the ultraviolet-visible-near infra-red region, a N,N-dimethylformamide solution of the $(NR_4)^+$ salt (wherein R was $C_2H_5$) displayed peaks at 825 nm (400), 645 nm (6,600), 545 nm (5,300), 453 nm and at 394 nm (19,500), where the numbers in parentheses are molar extinction coefficients in units of liter mole$^{-1}$ cm$^{-1}$. The complex $(NR_4)_3[Co(MoS_4)_2]$ wherein $R=C_2H_5$ displayed a magnetic moment of 3.3 BM as determined by the Evans NMR method.

Inasmuch as compounds containing the cobalt bis(tetrathiomolybdate) trianion of this invention are sensitive to oxygen, they must be maintained under non-oxidizing and preferably anaerobic conditions.

Powder X-ray data for the tetraethylammonium cobalt bis(tetrathiomolybdate), $[N(C_2H_5)_4]_3[Co(MoS_4)_2]$, are set forth in the Table for the major peaks in the powder pattern, that is for all peaks whose intensity was at least 10% of the most intense peak. This pattern indicates that the complex is isomorphous [N(C₂H₅)₄]₃[Fe(MoS₄)₂] and hence has a tetrahedrally coordinated central Co atom.

The invention will be more readily understood by reference to the following examples. In all cases the experiments were carried out under inert atmospheres.

EXAMPLES

EXAMPLE 1

1.3 ml of HSC₆H₅ and 1.75 ml of N(C₂H₅)₃ were added to a suspension of 0.669 g of CoCl in CH₃CN. The resulting green solution was added to a suspension of 4.9 g of [N(C₂H₅)₄]MoS₄·CH₃CN. The mixture was stirred and a dark green solution gradually resulted. Within 30 minutes, the reaction was completed and the solution was filtered. The product, [N(C₂H₅)₄][Co(MoS₄)₂] was precipitated by adding diethylether to the filtrate. The precipitated product was filtered, washed with diethylether, methanol and diethylether again. One gram of this catalyst precursor was pressed under 15,000–20,000 psi and then sieved through 10/20 mesh or 20/40 mesh sieves. One gram of this meshed catalyst precursor was mixed with 10 g of 1/16-in. spheroid porcelain beads and placed in the catalyst basket of a Carberry-type autoclave reactor. The remainder of the basket was filled with more beads. The reactor was designed to allow a constant flow of hydrogen through the feed and to permit liquid sampling during operation.

After the catalyst precursor and beads were charged to the reactor, the reactor system was flushed with helium for about 30 minutes after which hydrogen flow through the reactor was initiated at a rate of 100 cc/min. After the hydrogen began flowing through the reactor, the reactor was charged with 100 cc of a feed comprising a DBT/Decalin mixture which was prepared by dissolving 4.4 g of dibenzothiophene (DBT) in 100 cc of hot Decalin. The solution thus contained about 5 wt. % DBT of 0.8 wt. % S. The hot feed solution was filtered and 1 cc of decane was added.

After the feed was charged to the reactor, the hydrogen pressure was increased to about 450 psig and the temperature in the reactor raised from room temperature to about 350° C. over a period of about ½ hour during which time the catalyst was formed in-situ in the reactor. The hydrogen flow rate through the reactor was maintained at about 100 cc per minute. When the desired temperature and pressure was reached, a GC sample of liquid was taken and additional samples taken at one hour intervals thereafter. The liquid samples from the reactor were analyzed using a Gow Mac Series 550 Gas Chromatograph.

As the reaction progressed, samples of liquid were withdrawn once an hour and analyzed by GC chromatography in order to determine the activity of the catalyst towards hydrodesulfurization as well as its selectivity for hydrogenation. The hydrodesulfurization activity was determined according to the following model reaction:

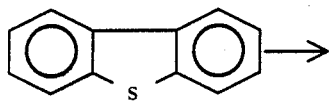

DBT
dibenzethiophene

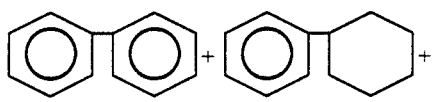

BP
biphenyl

CHB
cyclohexyl benzene

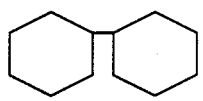

BC
bicyclohexyl
+ H₂S

The hydrodesulfurization zero order rate constant, r, for the catalyst was found to be $370 \times 10^{16}$ molecules of DBT desulfurized per gram of MoS₂ in the catalyst per second as shown in the Table. This rate is significantly higher than that of a catalyst formed from (NH₄)₂MoS₄ and tested in a similar manner which had a rate constant, r, of $45 \times 10^{16}$.

EXAMPLE 2

The Co complex, [N(C₂H₅)₄]₂[Co(WS₄)₂], was prepared in a manner similar to that described by Callahan and Piliero for the preparation of Ni(WS₄)₂²⁻. Thus CoCl₂·6H₂O (1.54 g) in a mixture of 40 ml water and 40 ml CH₃CN was acidified with about 4 ml glacial acetic acid. This solution was deaerated with argon gas for about 5–10 mins. after which it was added, dropwise, to a similarly deaerated, stirred solution of 4.34 g (NH₄)₂WS₄ in 160 ml of a 1:1 mixture of CH₃CN/H₂O. A black solution formed. After addition was completed, 6 g. [N(C₂H₅)₄]Br in 60 ml of a 1:1 mixture of CH₃CN/H₂O (deaerated with argon) was added to the black solution. A brown crystalline precipitate of [N(C₂H₅)₄]₂[Co(WS₄)₂] formed. After stirring for 30 minutes at 0° C., the product, [N(C₂H₅)₄]₂[Co(WS₄)₂], was filtered under argon, washed with water, then methanol followed by diethyl ether and air dried. The yield was 5.3 g (89%).

A catalyst was formed in-situ and its activity was measured using the same procedure described in Example 1. The resulting in-situ formed catalyst had a rate constant of $167 \times 10^{16}$ molecules of DBT converted/sec.-gm of WS₂ as shown in the Table. This example shows that compounds containing the bis(tetrathiotungstate) dianion are useful precursors for forming the catalysts of this invention.

EXAMPLE 3

This reaction was carried out in an inert atmosphere box. A N,N-dimethylformamide (10 ml) solution containing 0.180 g (1 mmol) of (n-C₅H₅)Co(CO)₂ was added to a mixture of 0.260 g (1 mmol) of (NH₄)₂MoS₄ and 1.05 g (5 mmol) of [N(C₂H₅)₄]Br in an inert atmosphere box at room temperature and stirred for three days after which 30 ml of diethylether was added to the reaction mixture and the precipitate formed was filtered. The precipitate was washed with methanol, then diethylether resulting in a 65% yield of the product [N(C₂H₅)₄]₃[Co(MoS₄)₂] as a dark olive-green powder (identical in spectroscopic properties to that of Examples 6 and 7).

EXAMPLE 4

Fifteen ml of a solution of $CoCl_2$ (0.027 g), $(C_2H_5)_3N$ (0.11 ml) and $C_6H_5SH$ (0.085 ml) in $CH_3CN$ was added to a solution of 0.27 g of $[(CH_3)_3NCH_2C_6H_5]_2MoS_4$ in 10 ml of $CH_3CN$ under anaerobic conditions over a period of 15 minutes. The product was filtered off anaerobically after 2 hours, and washed with 5:1 $C_2H_5OC_2H_5/CH_3CN$ and then with $C_2H_5OC_2H_5$ and dried in vacuum. The yield of $[(CH_3)_3NCH_2C_6H_5]_3[Co(MoS_4)_2]$ product was 90% of the theoretically calculated value.

EXAMPLE 5

To 30 ml of $CH_3CN$, 0.052 g (0.4 mmole) of $CoCl_2$ was added giving a blue solution. Thiophenol 1.6 mmol (0.16 ml) was added to this blue solution followed by the addition of 1.6 mmol (0.22 ml) of $N(C_2H_5)_3$, whereupon the solution turned dark green. This green solution was added to a solution of $(Y)_2MoS_4$, 0.8 mmol (1.04 g), in $CH_3CN$ over a period of 30 minutes. After 3 hr. 25 ml of dry $(C_2H_5)_2O$ was added to precipitate $(Y)_3[Co(MoS_4)_2]$. $(Y=[(C_6H_5)_3PNP(C_6H_5)_3]^+)$.

EXAMPLE 6

1.3 ml of HSC H and 1.75 ml of $N(C_2H_5)_3$ were added to a suspension of 0.669 g of $CoCl_2$ in $CH_3CN$. The resulting green solution was added to a suspension of 4.9 g of $[N(C_2H_5)_4]_2MoS_4$ in $CH_3CN$. The mixture was stirred and a dark green solution gradually resulted. Within 30 minutes the reaction was completed and the solution was filtered. The product was precipitated by adding diethylether to the filtrate. This experiment was repeated a number of times with product yields upward of 70% obtained in each case. The calculated values for $[(N(C_2H_5)_4]_3[Co(MoS_4)_2]$ product were C, 32.1%; H, 6.73% and N, 4.68%. The actual analytical results of C, H and N analysis for the product, C, 32.3%; H, 6.63%; and N, 4.55%, were in excellent agreement with the calculated values.

EXAMPLE 7

A mixture of 0.154 g (0.591 mmol) of $(NH_4)_2MoS_4$, 0.150 g (0.295 mmol) of $Co[S_2CN(C_2H_5)_2]_3$ and 0.621 g (2.95 mmol) of $[N(C_2H_5)_4]Br$ in 10 ml of degassed N,N-dimethylformamide was stirred under argon at 70° C. for 20 hr. after which 20 ml of degassed diethylether was added to the reaction mixture. The precipitate formed was filtered, washed with diethylether, methanol and diethylether again giving a 38% yield of the product, $[N(C_2H_5)_4]_3[Co(MoS_4)_2]$, as a dark green powder (identical in spectroscopic properties to that of Example 1).

| HDS ACTIVITY OF THIOHETEROANION DERVIED CATALYSTS | | | |
|---|---|---|---|
| Example # | Precursor | % $MS_2$[1] | Activity × $10^{-16}$/gm Precursor[2] | Activity × $10^{-16}$/gm $MS_2$ |
| 1 | $[N(C_2H_5)_4]_3Co(MoS_4)_2$ | 35.7 | 167 | 468 |
| 2 | $[N(C_2H_5)_4]_2Co(WS_4)_2$ | 52.6 | 88 | 167 |

[1]Amount of MS (M is, Mo or W) Contained in the precursor in percent.
[2]The activity is in molecules of DBI converted per sec per gm. precursor.

| Powder X-ray Diffraction Data For $[N(C_2H_5)_4]_3[Co(MoS_4)_2]$ | |
|---|---|
| d(Å) | I (relative) |
| 12.883 | 18.14 |
| 8.613 | 51.27 |
| 8.081 | 100.00 |
| 6.379 | 15.61 |
| 5.961 | 13.72 |
| 4.958 | 54.87 |
| 4.808 | 83.48 |
| 4.316 | 46.11 |
| 3.854 | 18.67 |
| 3.559 | 23.18 |
| 3.102 | 13.72 |
| 2.940 | 12.82 |
| 2.063 | 12.38 |
| 1.906 | 10.30 |

What is claimed is:

1. The composition of matter containing the $[Co(MoS_4)_2]^{3-}$ trianion of the structure

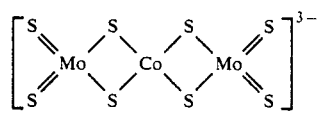

and one or more cations with a charge sufficient to balance the trinegative charge of said trianion.

2. The composition of matter of the formula $[(Cat^n)_{3/n}][Co(MoS_4)_2]$ wherein the $[Co(MoS_4)]^{3-}$ trianion has the structure

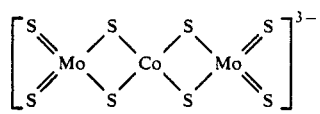

wherein the cobalt is in the 1+ oxidation state and wherein Cat is a mono, di or trivalent cation and n is 1, 2 or 3, respectively.

3. The composition of matter of the formula $[(Cat^n)_{3/n}][Co(MoS_4)_2]$ wherein the cobalt is tetrahedrally coordinated with four sulfur atoms with each of the two tetrathiomolybdate groups providing two of said four sulfur atoms, wherein Cat is a mono, di or trivalent onium cation and wherein n is 1, 2 or 3, respectively.

4. The composition of claim 3 wherein Cat is defined by the formula $[NH_aR_{4-a}]$ wherein R comprises an alkyl group, aryl group or mixture thereof and wherein a is 0, 1, 2, 3 or 4.

5. The composition of claim 4 wherein Cat is monovalent.

6. The composition of claim 5 wherein R is an alkyl group.

7. The composition of claim 6 wherein Cat is a monovalent, tetraalkyl ammonium cation.

8. The composition of claim 3 wherein Cat is defined by the formula $[XH_aR_{4-a}]$ wherein R comprises an alkyl group, aryl group and mixture thereof, wherein a is 0, 1, 2, 3 or 4 and wherein X is selected from the group consisting of P, As and mixture thereof.

9. The composition of claim 8 wherein X is P or As and R comprises an aryl group.

10. The composition of claim 3 wherein Cat is selected from the group consisting of $SOH_bR_{3-b}$ and $SH_bR_{3-b}$ wherein b is 0, 1, 2 or 3 and R is an alkyl group, aryl group and mixtures thereof.

11. The composition of claim 10 wherein R is an aryl group.

12. The composition of claim 1 wherein one or more monovalent cobalt compounds comprise one of the materials from which said compounds are formed.

13. The composition of claim 1 wherein one or more di or trivalent cobalt compounds comprise one of the starting materials and wherein the compositions are formed in the presence of sufficient reducing reagent for the cobalt to be converted to the monovalent form.

14. The compositions of either of claims 12 or 13 formed under anaerobic conditions.

15. The composition of either of claims 3, 1 or 2 formed in non-aqueous media under an inert atmosphere.

* * * * *